(12) United States Patent
Antebi et al.

(10) Patent No.: US 9,133,109 B2
(45) Date of Patent: Sep. 15, 2015

(54) METHOD FOR PREPARING BROMOUREA

(75) Inventors: Shomo Antebi, Haifa (IL); David Feldman, Haifa (IL)

(73) Assignee: Bromine Compounds Ltd., Beer-Sheva (IL)

( * ) Notice: Subject to any disclaimer, the term of this patent is extended or adjusted under 35 U.S.C. 154(b) by 74 days.

(21) Appl. No.: 13/823,757

(22) PCT Filed: Sep. 19, 2011

(86) PCT No.: PCT/IL2011/000740
§ 371 (c)(1),
(2), (4) Date: Mar. 15, 2013

(87) PCT Pub. No.: WO2012/038954
PCT Pub. Date: Mar. 29, 2012

(65) Prior Publication Data
US 2013/0178532 A1    Jul. 11, 2013

Related U.S. Application Data

(60) Provisional application No. 61/384,953, filed on Sep. 21, 2010.

(51) Int. Cl.
*C07C 273/18*    (2006.01)
*A01N 47/28*    (2006.01)
*A01N 33/08*    (2006.01)

(52) U.S. Cl.
CPC .......... *C07C 273/1863* (2013.01); *A01N 33/08* (2013.01); *A01N 47/28* (2013.01)

(58) Field of Classification Search
CPC ... A01N 33/08; A01N 47/28; C07C 273/1863
USPC .............................................. 564/32; 514/588
See application file for complete search history.

(56) References Cited

U.S. PATENT DOCUMENTS

| 6,322,822 | B1 | 11/2001 | Moore, Jr. |
| 6,423,267 | B1 | 7/2002 | Yang |
| 6,478,972 | B1 * | 11/2002 | Shim et al. ............ 210/755 |
| 2005/0147528 | A1 | 7/2005 | Shim |

FOREIGN PATENT DOCUMENTS

WO    2010143183 A2    12/2010

OTHER PUBLICATIONS

Grobe et al., Role of dose concentration in biocide efficacy against *Pseudomonas aeruginosa* biofilms; Journal of Industrial Microbiology & Biotechnology (2002) 29, 10-15.
Preliminary Report of Patentability of corresponding PCT application—7 pages—mailed Mar. 26, 2013.

* cited by examiner

*Primary Examiner* — Paul A Zucker
*Assistant Examiner* — Mark Luderer
(74) *Attorney, Agent, or Firm* — Roach Brown McCarthy & Grober, P.C.; Kevin D McCarthy

(57) ABSTRACT

The invention provides a process for manufacturing biocidal compositions containing bromourea derivatives, including the reaction of salts or adducts of the urea derivatives with an oxidizer.

20 Claims, No Drawings

METHOD FOR PREPARING BROMOUREA

REFERENCE TO CO-PENDING APPLICATIONS

Priority is claimed as a 371 of international application number PCT/IL2011/000740, filed on Sep. 19, 2011; which claims priority to U.S. provisional patent application Ser. No. 61/384,953, filed on Sep. 21, 2010.

FIELD OF THE INVENTION

The present invention relates to aqueous bromourea and chlorourea solutions and to stable precursor compositions thereof, as well as to methods for their preparation.

BACKGROUND OF THE INVENTION

The preparation of bromourea as a biocide solution was described previously, and it employed the direct bromination of a concentrated solution of urea with $Br_2$. Although the bromourea prepared by this method showed significant biocidal activity, it had only limited stability, especially under elevated temperatures. A chlorourea solution can be prepared via the chlorination of a concentrated urea solution and transported to the treatment site, where the bromourea solution can be prepared by mixing the chlorourea solution with an equimolar amount of NaBr (based on the total $Cl_2$). However, even the chlorourea has only limited stability at higher temperatures. It is therefore an object of this invention to provide an alternative technology providing stock solutions with increased stability to be transported to the desired treatment site and to be employed in forming a bromourea solution in situ, without the drawbacks of the previous materials and methods.

It is another object of the invention to provide a method for manufacturing a bromourea derivative solution on the site of need, comprising combining at least two aqueous solutions having a stability sufficiently high to be safely transported to the site of need.

It is still another object of the invention to provide a solution of bromourea derivative on the site of need, comprising reacting at least two aqueous streams comprising at least two reactants of relatively high stability.

Other objects and advantages of present invention will appear as description proceeds.

SUMMARY OF THE INVENTION

The invention provides a method for manufacturing a bromourea derivative, comprising reacting a salt or adduct of a urea derivative of the general structure A-U, where A stands for an acid and U stands for the urea derivative, with an oxidizer, while combining aqueous solutions of said urea derivative, of said acid, and of said oxidizer, wherein said urea derivative is in a molar excess over said acid, and the molar ratio of said acid to said oxidizer is at least 1.0. Said urea derivative is in at least four fold molar excess over said acid and at least ten fold excess over said oxidizer. Preferably, said urea derivative is in about fifteen fold molar excess over said acid, wherein said molar ratio of said acid to said oxidizer is at least 2.0. In a preferred embodiment, the method of invention for manufacturing a bromourea derivative comprises reacting a salt or adduct of the general structure A-U with an oxidizer, where A stands for HCl or HBr, and wherein U stands for urea. In a preferred embodiment of the invention, A stands for HCl, and the method comprises i) reacting said salt or adduct with NaOCl, thereby forming chlorourea, and adding to said chlorourea a solution comprising NaBr, thereby obtaining a composition comprising bromourea. In other preferred embodiment, A stands for HBr or a mixture of HBr with HCl, and the method comprises reacting said salt or adduct with NaOCl, thereby forming bromourea, and obtaining a composition comprising bromourea. Said oxidizer may be selected, for example, from NaOCl, LiOCl, $Ca(OCl)_2$, $ClO_2$, ozone, urea hydroperoxide, hydrogen peroxide, hydrogen peroxide precursors, percarbonates, perborates, peracetates or peroxycarboxylic acids, persulfates, and electrolytically prepared species. In a preferred embodiment, the method according to the invention comprises combining at least two liquid streams, one of which comprises an aqueous solution of said oxidizer. In another preferred embodiment, the method comprises combining at least two liquid streams, one of which comprises an aqueous solution of urea hydrochloride or urea hydrobromide. In still another preferred embodiment, the method according to the invention comprises combining at least two liquid streams, one of which comprises chlorourea or NaOCl. In a further preferred embodiment, the method according to the invention comprises combining at least two liquid streams, one of which comprises an aqueous solution containing bromide anion.

The invention is directed to a method, comprising i) reacting a salt or adduct of urea of the general structure A-U, where A stands for HCl and U stands for urea with an oxidizer comprising NaOCl, while stirring a mixture comprising urea, HCl, and NaOCl, wherein said urea is in a molar excess over said HCl, and said HCl is in a molar excess over said NaOCl, thereby providing a mixture comprising chlorourea; and ii) reacting said mixture comprising chlorourea with a bromide source, thereby providing a mixture comprising bromourea. In another aspect, the method according to the invention comprises i) electrolytically treating a salt or adduct of urea of the general structure A-U, where A stands for HCl or HBr, and U stands for urea, thereby providing a mixture comprising chlorourea or bromourea; and optionally ii) reacting said mixture with a bromide source thereby converting said chlorourea to bromourea.

The invention provides a biocidal composition comprising an aqueous solution containing a partially brominated urea derivative, wherein the non brominated part of said urea derivative is in at least four fold molar excess over the brominated part of said urea derivative. Said biocidal composition may be obtained in a process comprising reacting a salt or adduct of said urea derivative of the general structure A-U, where A stands for an acid and U stands for said urea derivative, with an oxidizer in a mixture containing said urea derivative, said acid, and said oxidizer, wherein said urea derivative is in at least four fold molar excess over said acid and in at least ten fold molar excess over said oxidizer. Said biocidal composition may be obtained in a process comprising reacting a salt or adduct of urea of the general structure A-U, where A stands for acid selected from HCl or HBr, and U stands for urea, with an oxidizer comprising NaClO in a mixture containing urea, said acid, and said oxidizer, wherein said urea is in at least ten fold molar excess over said acid and in at least twenty fold molar excess over said oxidizer. Said biocidal composition preferably comprises an aqueous mixture of an urea derivative, brominated urea derivative, and chloride, wherein said urea derivative is in at least ten fold molar excess over said brominated urea derivative, and in at least ten fold molar excess over said chloride. In a preferred embodiment of the invention, said biocidal composition comprises an aqueous mixture of urea, bromourea, and chloride, wherein said urea is in at least ten fold molar excess over said brominated derivative, and in at least ten fold molar excess over said chloride. The biocidal composition of the invention preferably comprises bromourea obtained by reacting aqueous urea with a hydrohalic acid and sodium hypochlorite in a molar excess of urea over the acid of at least 10.

The invention is directed to a method of cleaning industrial and agricultural equipment, comprising contacting the surfaces or volumes to be cleaned with an aqueous composition containing a partially brominated urea derivative, wherein the non brominated part of said urea derivative is in at least four fold molar excess over the brominated part of said urea derivative. The invention relates to the use of an aqueous composition containing a partially brominated urea derivative, wherein the non brominated part of said urea derivative is in at least four fold molar excess over the brominated part of said urea derivative, in cleaning an industrial and agricultural equipment, particularly irrigation pipes.

DETAILED DESCRIPTION OF THE INVENTION

It has now been found that oxidizing certain urea salts provides an alternative method in preparing chlorourea and bromourea or their analogs. This invention enables to manufacture bromourea in a method comprising reacting a urea salt or adduct of the general structure A-U, where A stands for an acid and U stands for urea, with an oxidizer, while mixing and eventually cooling the mixture, wherein the molar ratio of said acid to said oxidizer is at least 1.0 and wherein the molar ratio of said urea to said oxidizer is at least 1.0. The acid is, in one preferred embodiment, HCl when producing chlorourea, which chlorourea can be converted to bromourea by reacting with a bromide source; the acid may comprise HBr, or a mixture of HCl and HBr, or a mixture of HBr with any other acid, when directly producing bromourea. Said oxidizer is preferably selected from NaOCl, LiOCl, $Ca(OCl)_2$, $ClO_2$, ozone, urea hydroperoxide, hydrogen peroxide, hydrogen peroxide precursors, percarbonates, perborates, peracetates and peroxycarboxylic acids, persulfate (oxone), and electrolytically prepared species. For example, bromourea may be electrochemically prepared from A-U where A is HBr; alternatively, bromourea may be prepared by electrochemical conversion of A-U where A is HCl to chlorourea, followed by contacting with an NaBr solution. There is a possibility to obtain halourea by electrochemical means, wherein NaOCl or NaOBr formed electrochemically from NaCl or NaBr, respectively, is reacted with A-U, where A stands for an acid like HCl or HBr, and U stands for urea.

The invention provides a method for manufacturing a bromourea derivative, comprising reacting a salt or adduct of a urea derivative of the general structure A-U, where A stands for an acid and U stands for the urea derivative, with an oxidizer, while combining or mixing aqueous solutions of said urea derivative, of said acid, and of said oxidizer, wherein said urea derivative is in a molar excess over said acid, and the molar ratio of said acid to said oxidizer is at least 1.0. Said urea derivative is in at least four fold molar excess over said acid and at least ten fold excess over said oxidizer, wherein said molar ratio of said acid to said oxidizer is at least 1.0. In a preferred embodiment of the invention, said urea derivative is in at least fifteen fold molar excess over said acid, wherein said molar ratio of said acid to said oxidizer is at least 2.0. In a preferred embodiment of the invention, provided is a method for manufacturing a bromourea derivative comprising reacting a salt or adduct of the general structure A-U, where A stands for HCl or HBr, and wherein U stands for urea. In one aspect of the invention, said A stands for HCl, and the method comprises i) reacting said salt or adduct with NaOCl, thereby forming chlorourea, and ii) adding to said chlorourea a solution comprising NaBr, thereby obtaining a composition comprising bromourea. In another aspect of the invention, said A stands for HBr or a mixture of HBr with HCl, comprising reacting said salt or adduct with NaOCl, resulting in the formation of bromourea and in obtaining a composition comprising bromourea. Said oxidizer is preferably selected from NaOCl, LiOCl, $Ca(OCl)_2$, $ClO_2$, ozone, urea hydroperoxide, hydrogen peroxide, hydrogen peroxide precursors, percarbonates, perborates, peracetates or peroxycarboxylic acids, persulfates, and electrolytically prepared species. The method of the invention comprises, in a preferred embodiment, contacting or mixing of at least two liquid streams, one of which comprises an aqueous solution of said oxidizer. In one aspect of the invention, provided is a method for manufacturing a brominated urea derivative, comprising mixing at least two liquid streams, a first stream comprising an aqueous solution of an adduct or salt of a urea derivative of the general structure A-U, where A stands for HBr, HCl, or a mixture thereof, and U stands for a urea derivative, a second stream comprising an oxidizer. In one embodiment of the invention, the method comprises mixing two streams, a first stream comprising a urea derivative of the general structure A-U where A stands for HBr, and a second stream comprising an oxidizer. In another embodiment of the invention, the method comprises mixing three streams, a first stream comprising a urea derivative of the general structure A-U where A stands for HCl, a second stream comprising an oxidizer, and a third stream comprising bromide anion. In another aspect of the invention, provided is a method for manufacturing bromourea, comprising mixing three liquid streams, a first stream comprising an aqueous solution of an adduct or salt of urea of the general structure A-U, where A stands for an acid other than HBr, and U stands for urea, a second stream comprising an oxidizer, and a third stream comprising bromide ion. In a still other aspect of the invention, provided is a method for manufacturing bromourea, comprising mixing at least two liquid streams, one of the streams comprising an aqueous solution of an adduct or salt of urea of the general structure A-U, where A stands for HBr, HCl, or a mixture thereof, and U stands for urea. In a preferred embodiment of the invention, the method comprises mixing two streams, a first stream comprising an adduct or salt of urea of the general structure A-U where A stands for HBr, and a second stream comprising an oxidizer. In another preferred embodiment of the invention, the method comprises mixing three streams, a first stream comprising an adduct or salt of urea of the general structure A-U where A stands for HCl, a second stream comprising an oxidizer, and a third stream comprising bromide anion. In a preferred embodiment, the method comprises contacting at least two liquid streams, a first stream comprising an aqueous solution of urea hydrobromide in an excess of urea, and a second stream comprising hypochlorite. In other preferred embodiment of the invention, the method comprises mixing three aqueous streams one of which comprises urea hydrochloride, another one comprises hypochlorite, and the third one comprises bromide anion. In a preferred embodiment, the invention is directed to a method for manufacturing bromourea, comprising mixing two aqueous streams, one comprising a salt or adduct of urea of the general structure A-U and the other comprising NaOCl, where A stands for an acid being either HBr or a mixture of HBr with HCl, and U stands for urea, wherein said urea is in a molar excess over said acid, and said acid is in a molar excess over said NaOCl. In another aspect of the invention, provided is a method for manufacturing a bromourea derivative, comprising i) electrolytically treating a salt or adduct of urea of the general structure A-U, where A stands for HCl or HBr, and U stands for urea, thereby providing a mixture comprising chlorourea or bromourea; and if A does not comprise a bromide source ii) reacting said mixture with a bromide source thereby converting said chlorourea to bromourea. When relating to a salt or adduct of urea or urea derivative of the general structure A-U, intended is an equimolar mixture of urea or its derivative with an acid having formula A; in the preferred embodiments of the invention, said salt or adduct is present in the aqueous solution in the presence of an excess of free urea. The term bromourea derivative aims at the same chemical entity as the term brominated urea derivative. The invention relates to a bromourea derivative composition comprising an aqueous solution in which a part of said urea derivative is brominated and a part is not, wherein the non brominated part of said urea derivative is in at least five fold, and preferably in at least ten fold molar excess over the brominated part of said urea derivative. Said brominated urea derivative is preferably obtained in a process comprising reacting a salt or adduct of said urea derivative of the general structure A-U, where A stands for an acid and U stands for said urea derivative, with an oxidizer in a mixture containing said urea derivative, said acid, and said oxidizer, wherein said urea derivative is in at least ten fold molar excess over said acid and in at least twenty fold molar excess over said oxidizer. Said brominated urea derivative is preferably obtained in a process comprising reacting a salt or adduct of urea derivative of the general structure A-U, where A stands for acid selected from HCl or HBr, and U stands for urea derivative, particularly urea, with an oxidizer comprising NaClO in a mixture containing urea derivative, particularly urea, and further containing said acid and said oxidizer, wherein said urea derivative is in at least ten fold molar excess over said acid and in at least twenty fold molar excess over said oxidizer. The invention aims at providing a biocidal composition comprising a urea derivative that is partially brominated, comprising an aqueous mixture containing said urea derivative in non-brominated form, said urea derivative in brominated form, and further chloride, wherein said non-brominated form is in at least three fold molar excess, preferably in at least ten fold molar excess over said brominated form, and in at least three fold molar excess, preferably in at least ten fold molar excess over said chloride. In a preferred embodiment of the invention, said brominated urea derivative composition comprises an aqueous mixture of urea, bromourea, and chloride, wherein said urea is in at least three fold molar excess, preferably in at least ten fold molar excess over said bromourea, and in at least three fold molar excess, preferably in at least ten fold molar excess over said chloride. The invention provides a method of cleaning industrial and agricultural equipment, comprising contacting the surfaces or volumes to be cleaned with an aqueous composition containing a partially brominated urea derivative, wherein the non brominated part of said urea derivative is in at least four fold molar excess over the brominated part of said urea derivative. The invention is directed to the use of said aqueous composition for cleaning an industrial and agricultural equipment, particularly irrigation pipes.

In a preferred embodiment, the method of the invention comprises mixing/contacting at least two liquid streams, one of which comprises an aqueous solution of said oxidizer. Said streams may comprise an aqueous solution of urea hydrochloride or urea hydrobromide. In a preferred embodiment, said streams may comprise an aqueous solution containing bromide anions, such as ions originating from a bromide or hydrobromic acid or other bromide sources, which bromide ions react with a stable chlorourea solution as prepared from said adduct of urea and hydrochloric acid, A-U, and NaOCl.

The invention relates to a bromourea solution manufactured according to the above superior method.

The new method for the production of bromourea was developed in order to avoid a direct chlorination of urea with $Cl_2$ gas and in order to make its use in the field easier on the application site by using more stable stock solutions. Suitable stock solutions are combined on the site of the desired application to produce bromourea derivative or bromourea.

It is known that the reaction of NaOCl with urea easily results in the decomposition of urea to $N_2$ and $CO_2$. However, it was found that under certain conditions, particularly in an acidic environment, the decomposition may be inhibited. For example, urea salt, or salts of other urea derivatives like biuret, polyurea, or thiourea, having general structure HBU wherein H stands for hydrogen cations, wherein B is selected from $Cl^{-1}$, $Br^{-1}$, $SO_4^{-2}$, $PO_4^{-3}$, and other mono- or multivalent ions, and U stands for urea or its derivative, may be reacted with NaOCl under acidic conditions. It is believed that a comproportionation reaction of a halogen atom having valency −1 with a halogen atom having valency +1 in the presence of excessive urea or urea derivative provides a composition of superior biocidal qualities.

In a preferred embodiment, the invention employs a stable solution of urea hydrochloride, eventually with phosphoric acid or other acids. In another preferred embodiment, the invention employs a stable solution of urea hydrochloride, urea phosphate and alike in the presence of a bromide source. In a sill other preferred embodiment, the invention employs a stable solution of urea hydrobromide. Said stable solutions are combined with an oxidizer in situ, while adding a bromide source where missing. Preferably used stock solution is a solution of urea hydrobromide. Said solution may contain HBr and urea in any ratio. The amount of the added oxidizer (i.e. NaOCl) should not exceed the equivalent amount of acid that is introduced (i.e the molar ratio between HBr and NaOCl should be greater than or equal to 1). The molar ratio of urea to the acid may be, for example, between 4:1 and 50:1. The amount of urea is preferably in excess, up to the solubility level of urea in the aqueous solution. The invention comprises oxidation of a urea salt, which is stable and can be used as stock solution to be delivered to the treatment site. Said stable solution may comprise a urea hydrohalide which is mixed with an oxidizer (such as NaOCl) to form halogenurea. Said hydrohalide may be hydrochloride or hydrobromide, or a mixture of hydrobromide with other acid, to form chlorourea or bromourea, respectively.

The invention relates to a method comprising mixing of the chlorourea solution with NaBr (solid or solution, or any other bromide source such, HBr, ammonium bromide and the like) to form bromourea. An alternative method for the preparation of the bromourea solution is the parallel addition of an oxidizer (i.e. NaOCl) and an aqueous NaBr solution to a solution of urea hydrochloride. A still another alternative is mixing a solution comprising urea and NaBr with a solution of an oxidizer (i.e., NaOCl). Still another alternative for the preparation of bromourea comprises preparing urea hydrobromide by mixing aq. HBr solution (i.e. 48%) with urea, and then reacting this solution with NaOCl.

Preparing bromourea may involve the use of two streams or three streams of solutions. For example a bromourea solution can be obtained by mixing a urea hydrobromide salt as a first stream with an oxidizer as a second stream. An alternative method is to use three streams, i.e one stream of urea hydrochloride salt with NaOCl solution as a second stream together with a third stream of an NaBr solution. A still another alternative method uses two streams comprising a solution containing a urea hydrochloride salt, and NaBr as a first stream with a solution of an oxidizer (i.e., NaOCl) as a second stream. Said oxidizers, in all above cases, may comprise LiOCl, Ca(OCl)$_2$, ClO$_2$, ozone, urea hydroperoxide, hydrogen peroxide or its precursors, percarbonates, perborates, peracetates and peroxycarboxylic acids, persulfate (oxone), electrolytically prepared species, and the like.

The invention relates to bromourea derivatives and to methods of their preparation from urea derivatives by bromination, without employing elemental chlorine or bromine. The method of the invention comprises reacting a salt or adduct of a urea derivative of the general structure A-U, where A stands for an acid and U stands for the urea derivative, with an oxidizer, while stirring a mixture comprising said urea derivative, said acid, and said oxidizer, wherein said urea derivative is preferably in a molar excess over said acid and over said oxidizer. Said reaction mixture does not comprise elemental chlorine or bromine, and preferably comprises a bromide as the source of bromine for brominating said urea derivative, the bromide comprising, for example, sodium bromide, hydrogen bromide or ammonium bromide. In a preferred embodiment, said reaction mixture comprises NaOCl as the oxidizer. Said urea derivative to be brominated in the method of the invention may comprise compounds exhibiting some structural molecular features of urea, for example, polyurea, biuret, thiourea, and guanidine.

The method of the invention for manufacturing a bromourea, comprising reacting a urea salt or adduct A-U where A stands for an acid and U with oxidizer, may employ various modifications. In one aspect, the method of the invention may comprise mixing urea and HCl in water to obtain HCl—U adduct, oxidizing the adduct with NaOCl to obtain chlorourea, and adding a solution of NaBr to obtain bromourea. In accordance with the method of the invention, stable aqueous stock solutions may be brought to the treatment site before the formation of bromourea including, for example, a stock solution comprising urea and HCl or a stock solution comprising chlorourea. Stock solutions may comprise urea with HBr, or urea and HBr and other acid, or urea hydrochloride and sodium bromide. Other stock solutions may comprise, for example, aqueous acid and aqueous bromide. In another aspect of the invention, the method comprises mixing urea with HBr or with a mixture of HCl and HBr in water, and adding oxidizer, without employing bromide salt. The oxidant should be added slowly. Usually, the ratio between urea and oxidizer is at least 4:1, preferably at last 10:1, and the ratio between urea and the acid is preferably higher than 4, for example about 15, possibly up to 20 or more. The pH is usually between 1.15-2.3. The total amount of the acid in relation to the oxidizer is in one embodiment preferably 2.3:1. A more diluted oxidizer provides a higher yield of the oxidized product.

The invention provides a partially brominated urea derivative in an aqueous solution containing an amount of said derivative which is brominated and an amount which is non brominated, wherein the non brominated amount is in molar excess over the brominated amount. The brominated urea derivative is obtained by reacting a salt or adduct of said urea derivative of the general structure A-U, where A stands for an acid and U stands for said urea derivative, with an oxidizer in a mixture containing said urea derivative, said acid, and said oxidizer, wherein said urea derivative is preferably in at least three fold molar excess over said acid. In a preferred embodiment of the invention, said urea derivative is in at least five fold molar excess over said acid. Usually, higher excess provides higher oxidation yield. In various embodiments of the invention, said urea derivative is in about 5 fold molar excess over said acid, or in about 10 fold molar excess over said acid, or in about 15 fold molar excess over said, or in about 20 fold molar excess over said acid, or in about 25 fold molar excess over said acid or more. In a preferred embodiment, A stands for acid selected from HCl or HBr, and U stands for urea, while said oxidizer comprises NaClO. The reaction mixture may contain urea and acid in a molar ratio of at least 4, preferably between 10 and 20, for example about 15. When preparing a biocidal composition comprising bromourea according to the invention, the molar ratio of urea to the acid in the reaction mixture may be between 5 and 40, more typically between 10 and 20, for example about 15; the molar ratio of urea to the oxidizer in the reaction mixture may be between 5 and 50, more typically between 20 and 50, for example about 35. The final aqueous brominated urea derivative may comprise a urea derivative and its brominated form in a molar ratio of between 10 and 50. The aqueous biocidal composition of the invention comprising bromourea typically contains urea, bromourea, and sodium chloride, wherein the molar ratio of urea to bromourea is between 10 and 50, for example about 35, and the molar ratio of urea to sodium chloride is between 5 and 50. Said composition further contains residual acid, typically hydrochloric or hydrobromic, wherein the ratio of urea to the acid is for example between 20 and 40. The active bromine, measured as the total chlorine by iodometry, is preferably between 0.5 and 5%, usually more than 1%.

Thus, the invention relates to biocidal compositions comprising brominated urea derivatives, preferably bromourea, and to methods of their preparation from urea derivatives by bromination without employing elemental chlorine or bromine. In a preferred embodiment, the invention relates to a method comprising a step of oxidizing an urea salt or adduct, preferably in a stable aqueous solution, with NaOCl. In one preferred embodiment, the invention relates to a method comprising a step of mixing a chlorourea solution with NaBr.

EXAMPLES

Example 1

Preparation of Chlorourea Solution
(Urea:HCl:NaOCl Molar Ratio 36:2.2:1)

In a 250 ml round bottom flask equipped with a magnetic stir bar, a dropping funnel and a thermocouple, 46.04 g urea (Mw 60, 767 mmol) was dissolved in 35.3 g H$_2$O, followed by the addition (upon cooling, exothermic) of 5.37 g of 32% HCl (Mw 36.64, 46.9 mmol). To the solution was added upon cooling 13.3 g of an aq. 10.7% NaOCl solution (wt % as active Cl$_2$, 20 mmol) during 14 min. A slightly yellow solution was obtained retaining 1.27% Cl$_2$ (wt % as total Cl$_2$, iodometric titration, in relation to 1.5% wt % theoretical as Cl$_2$). UV analysis showed the typical absorption for chlorourea at 244 nm. The solution was stable for at least 1 week.

Example 2

Preparation of Bromourea Solution
(NaOCl:HCl:Urea:NaBr Molar Ratio 1:2.3:38:0.9)

In a 250 ml round bottom flask equipped with a magnetic stir bar, a dropping funnel and a thermocouple, 46.04 g urea (Mw 60, 767 mmol) was dissolved in 35.3 g H2O, followed by the addition (upon cooling, exothermic) of 5.37 g of 32% HCl (Mw 36.64, 46.9 mmol). To the solution was added upon cooling 13.4 g of an aq. 10.7% NaOCl solution (wt % as active Cl$_2$, 20.2 mmol) during 14 min. A slightly yellow solution was obtained retaining 1.24% $Cl_2$ (as total $Cl_2$, Iodometric titration, 1.46% theoretical). NaBr salt (1.8 g, 17.45 mmol) was added to the solution. The color of the solution changed from yellow to orange (pH 2.03), Example 3

Preparation of Bromourea Solution by Adding an Aqueous Solution of 10.7% NaOCl (wt % as Cl2) and a 38% Aqueous Solution of NaBr (wt %) to a Solution of Urea Hydrochloride
(NaOCl:HCl:Urea:NaBr Molar Ratio 1:2.2:37.7:0.8)

In a 250 ml round bottom flask equipped with a magnetic stir bar, a dropping funnel and a thermocouple, 46.04 g urea (Mw 60, 767 mmol) was dissolved in 30.6 g H2O, followed by the addition (upon cooling, exothermic) of 5.4 g of 32% HCl (Mw 36.64, 47.2 mmol). A solution of urea hydrochloride was obtained. 13.5 g of an aq. 10.7% NaOCl solution (wt % as Cl2, 20.3 mmol) placed in an addition funnel and 4.84 g of 38% NaBr solution was placed in another addition funnel. NaOCl solution was added to the urea hydrochloride solution and after a delay of 1 min. the 38% aqueous NaBr was added to the same solution. An orange solution was obtained, (pH 2.02), showing an absorption at 275 nm (UV), typical to bromourea. Iodometric titration detected 1.275% Cl2 (wt %, as total Cl2, 1.5% theoretical).

Example 4

Preparation of Bromourea Solution
(Urea:HBr:NaOCl Molar Ratio 36:2.6:1)

In a 250 ml round bottom flask equipped with a magnetic stir bar, a dropping funnel and a thermocouple, 46 g urea (Mw 60, 767 mmol) was dissolved in 31.8 g H2O, followed by the addition (upon cooling, exothermic) of 8.96 g of 48% HBr (Mw 80.92, 53.15 mmol). To the solution was added upon cooling 13.4 g of an aq. 10.7% NaOCl solution (wt %, as total Cl2, 20.2 mmol) during 10 min. An orange solution was obtained retaining 1% $Cl_2$ (wt %, as total $Cl_2$, iodometric titration, in relation to 1.43% theoretical). UV analysis showed the typical absorption for bromourea at 275 nm. The solution was stable for at least 24 hrs.

Example 5

Preparation of Bromourea Solution by Adding an Aqueous Solution of 10.9% NaOCl (wt %/wt % as Cl2) to a Solution Composed of 32% HCl (wt/wt %), 48% Aqueous HBr (wt %/wt %) and Urea
(NaOCl:HCl:HBr:Urea Molar Ratio 1:1.15:1.15:10.5)

Solution A: In a 100 ml flask, urea was dissolved (12.8 g, 213.5 mmol) in 79.8 g H2O, followed by the addition of 2.68 g of 32% HCl (23.5 mmol), and 3.95 g of 48% aqueous HBr (23.4 mmol).

Solution B: An NaOCl solution (1.66% wt %/wt % as Cl2) freshly prepared from 13.3 g of an aq. 10.9% NaOCl solution (wt %/wt % as Cl2, 20.4 mmol) diluted in 73.9 g H2O.

Solution A and solution B were added simultaneously during 24 min to a 250 ml round bottom flask containing H2O (14.4 g) and equipped with a magnetic stirrer.

An orange solution was obtained, (pH 1.34), showing an absorption at 274 nm (UV), typical to bromourea. Iodometric titration detected 0.64% Cl2 (wt %/wt %, as total Cl2, 0.72% being theoretical value).

Example 6

Biocidal Activity Against Simulated Biofilm Systems (Alginate Beads)

A biofilm simulation system, alginate beads, developed by the Biofilm Bozeman Institute Montana (Grobe, K. J, Zahller, J and Stewart P. S., 2002 in "Role of dose concentration in biocide efficacy against *Pseudomonas aeruginosa* Biofilms", J. Industrial Microbiology & Biotechnology, vol. 29, pp 10-15), was used in order to evaluate the efficacy of bromine/urea against biofilm.

Preparation of the Alginate Beads

The biofilm simulation was created by entrapping bacteria in alginate gel beads. A plate of R2A agar was streaked with *Pseudomonas aeruginosa* (ATCC 15442) and incubated at 35° C. overnight. Buffer phosphate at pH 7.2 was used to scrap off the bacteria from the agar plate and to create a suspension. The bacterial suspension was mixed with an equal volume of an aqueous 4% sodium alginate solution, to make a final 2% alginate solution. The alginate and bacterial slurry were placed in a 50 ml syringe attached to a gauge needle (22), connected to a compressed air tank, allowing the syringe be pressurized. At 20 psig pressure a stream of small drops was forced out and dropped into a stirred solution of 50 mM $CaCl_2$. The $Ca^{+2}$ cross linked the alginate, and semi solid beads with entrapped bacterial cells were formed. The beads were allowed to stir in the $CaCl_2$ solution for about 20 minutes, and then rinsed in a dilute 5 mM $CaCl_2$ solution. Several flasks containing 100 beads each were incubated overnight at 35° C. on a rotating shaker in a buffer solution (at pH 7) with 5 mM addition of $CaCl_2$ to maintain the beads structure. The resulting beads diameter is about 2 mm General Description of the Experiment At the beginning of the experiment, the supernatant of the beads buffer suspension containing 5 mM $CaCl_2$ was decanted and replaced by the 100 ml biocide solution with the required concentration. Chlorourea compositions prepared as in Example 1, and bromourera composition prepared as in Example 2, were used for the biocidal experiments. Urea-bromine compositions prepared by dissolving urea 15.02 g (250.3 mmol, 15% concentration) and 1.17 g $Br_2$ (7.32 mmol, 1.17% concentration) in 84 g $H_2O$ (34.2:1 urea:$Br_2$ molar ratio). After different interval contact times, 10 beads were removed and placed in a 5 g/l sodium thiosulfate solution containing 50 mM sodium citrate. The sodium citrate was used to dissolve the alginate gel and release the bacteria into the solution. The neutralizer-citrate solution was placed in the refrigerator for 2 hours, than diluted and placed on R2A agar plates using pour plate technique. The plates were incubated at 35° C. for 24-48 hours and counted. The efficacy and toxicity of the neutralizer were checked as well as a control experiment without biocide addition. Four concentrations (0.5, 1, 2.5 and 5 ppm) were tested at four different contact times (5, 15, 30, and 60 min). Table 1-2 describe the surviving colony forming units (CFU) of the bacteria after different biocides treatment at different contact times.

TABLE 1

Biocidal efficacy of bromourea against bacterial beads - survival of bacteria (CFU) as a function of biocide loading and contact time

| Contact time | Biocide concentration (ppm as $Cl_2$) | | | |
|---|---|---|---|---|
| | 0.5 | 1 | 2.5 | 5 |
| 0 | $9.22 \times 10^6$ | $9.22 \times 10^6$ | $9.22 \times 10^6$ | $9.22 \times 10^6$ |
| 5 | $8.10 \times 10^6$ | $9.30 \times 10^6$ | $2.72 \times 10^6$ | $3.00 \times 10^5$ |
| 15 | $8.00 \times 10^6$ | $1.73 \times 10^6$ | $6.08 \times 10^2$ | <1.00 |
| 30 | $3.50 \times 10^6$ | $1.00 \times 10^4$ | $5.00 \times 10^1$ | <1.00 |
| 60 | $7.37 \times 10^5$ | <1.00 | <1.00 | <1.00 |

TABLE 2

Biocidal efficacy of chlorourea against bacterial beads - survival of bacteria (CFU) as a function of biocide loading and contact time

| Contact time | Biocide concentration (ppm as $Cl_2$) | | | |
|---|---|---|---|---|
| | 0.5 | 1 | 2.5 | 5 |
| 0 | $2.28 \times 10^7$ | $2.28 \times 10^7$ | $2.28 \times 10^7$ | $2.28 \times 10^7$ |
| 5 | $2.80 \times 10^7$ | $1.89 \times 10^7$ | $2.20 \times 10^7$ | $2.16 \times 10^7$ |
| 15 | $2.43 \times 10^7$ | $1.61 \times 10^7$ | $1.42 \times 10^7$ | $1.00 \times 10^6$ |
| 30 | $2.28 \times 10^7$ | $1.66 \times 10^7$ | $3.56 \times 10^5$ | $3.25 \times 10^3$ |
| 60 | $1.00 \times 10^7$ | $6.40 \times 10^5$ | $1.58 \times 10^3$ | <1.00 |

While the invention has been described using some specific examples, many modifications and variations are possible. It is therefore understood that the invention is not intended to be limited in any way, other than by the scope of the appended claims.

The invention claimed is:

1. A method for manufacturing bromourea comprising
   (i) providing an aqueous solution comprising a salt or adduct of urea of the general structure A-U, where A stands for an acid selected from HBr or HCl and U stands for urea,
   (ii) providing an aqueous solution of an oxidizer, and
   (iii) combining at least two liquid streams, one of which comprises the solution provided in step (i) and the other one comprises the solution provided in step (ii) whereby forming bromourea or chlorourea and adding to said streams a solution comprising bromide source if said acid is HCl,
   thereby obtaining an acidic composition comprising said bromourea wherein said urea is in a molar excess over said acid, and the molar ratio of said acid to said oxidizer is at least 1.0, said solutions being stored as stable precursors and being optionally diluted before combining said streams in situ, and wherein the active bromine in the combined streams, measured as the total chlorine by iodometry is up to 5%.

2. The method according to claim 1, wherein said urea is in at least three fold molar excess over said acid and at least ten fold excess over said oxidizer.

3. The method according to claim 1, wherein said urea is in about fifteen fold molar excess over said acid, and wherein said molar ratio of said acid to said oxidizer is at least 2.0.

4. The method according to claim 1 where A stands for HCl, comprising
   i) reacting said salt or adduct with NaOCl, thereby forming chlorourea, and
   ii) adding to said chlorourea a solution comprising NaBr, thereby obtaining a composition comprising bromourea.

5. The method according to claim 1 where A stands for HBr or a mixture of HBr with HCl, comprising reacting said salt or adduct with NaOCl, thereby forming bromourea and obtaining a composition comprising bromourea.

6. The method according to claim 1, wherein said oxidizer is selected from NaOCl, LiOCl, $Ca(OCl)_2$, $ClO_2$, ozone, urea hydroperoxide, hydrogen peroxide, hydrogen peroxide precursors, percarbonates, perborates, peracetates or peroxycarboxylic acids, persulfates, and electrolytically prepared species.

7. The method according to claim 1, comprising combining at least two liquid streams, in any order, one of which comprises an aqueous solution of said oxidizer.

8. The method according to claim 1, comprising combining at least two liquid streams, in any order, one of which comprises an aqueous solution of urea hydrochloride or urea hydrobromide.

9. The method according to claim 1, comprising combining at least two liquid streams, in any order, one of which comprises chlorourea or NaOCl.

10. The method according to claim 1, comprising combining at least two liquid streams, in any order, one of which comprises an aqueous solution containing bromide anion.

11. The method according to claim 1, comprising
    i) reacting a salt or adduct of urea of the general structure A-U, where A stands for HCl and U stands for urea with an oxidizer comprising NaOCl, while stirring a mixture comprising urea, HCl, and NaOCl, wherein said urea is in a molar excess over said HCl, and said HCl is in a molar excess over said NaOCl, thereby providing a mixture comprising chlorourea; and
    ii) reacting said mixture comprising chlorourea with a bromide source, thereby providing a mixture comprising bromourea.

12. The method according to claim 1, comprising
    i) electrolytically treating a salt or adduct of urea of the general structure A-U, where A stands for HCl or HBr, and U stands for urea, thereby providing a mixture comprising chlorourea or bromourea; and optionally
    ii) reacting said mixture with a bromide source thereby converting said chlorourea to bromourea.

13. A biocidal and antibiofouling composition containing a bromourea manufactured according to claim 1, comprising urea partially in non-brominated form and partially in brominated form, wherein the non-brominated part of urea is in at least three fold molar excess over said brominated part of said urea.

14. The biocidal and antibiofouling composition according to claim 13, wherein said urea is in at least four fold molar excess over said acid and in at least ten fold molar excess over said oxidizer.

15. The biocidal and antibiofouling composition according to claim 13, obtained in a process comprising reacting a salt or adduct of urea of the general structure A-U, where A stands for acid selected from HCl or HBr, and U stands for urea, with an oxidizer comprising NaClO, in a mixture containing urea, said acid, and said oxidizer, wherein said urea is in at least ten fold molar excess over said acid and in at least twenty fold molar excess over said oxidizer.

16. The biocidal and antibiofouling composition according to claim 13, comprising an aqueous mixture of urea, brominated urea, and chloride, wherein said urea is in at least ten fold molar excess over said brominated urea, and in at least ten fold molar excess over said chloride.

17. The biocidal and antibiofouling composition according to claim 13, comprising an aqueous mixture of urea, bromourea, and chloride, wherein said urea is in at least fifteen fold molar excess over said bromourea, and in at least fifteen fold molar excess over said chloride.

18. The biocidal and antibiofouling composition according to claim 13 comprising bromourea obtained by reacting aqueous urea with a hydrohalic acid and sodium hypochlorite in a molar excess of urea over the acid of at least 10.

19. A method of cleaning industrial equipment, irrigation pipes, and agricultural equipment, comprising contacting the surfaces or volumes to be cleaned with a biocidal and antifouling composition according to claim 14.

20. The method according to claim 1 wherein the pH in the combined streams is from 1.15 to 2.3.

* * * * *